US011529054B2

United States Patent
Mariano et al.

(10) Patent No.: US 11,529,054 B2
(45) Date of Patent: Dec. 20, 2022

(54) METHOD AND SYSTEM FOR POST-TRAUMATIC STRESS DISORDER (PTSD) AND MILD TRAUMATIC BRAIN INJURY (MTBI) DIAGNOSIS USING MAGNETIC RESONANCE SPECTROSCOPY

(71) Applicant: The Charles Stark Draper Laboratory, Inc., Cambridge, MA (US)

(72) Inventors: Laura J. Mariano, Somerville, MA (US); John M. Irvine, Somerville, MA (US); Nirmal Keshava, Cambridge, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 628 days.

(21) Appl. No.: 16/044,874

(22) Filed: Jul. 25, 2018

(65) Prior Publication Data

US 2020/0029815 A1   Jan. 30, 2020

(51) Int. Cl.
*G16H 50/20* (2018.01)
*G16H 30/40* (2018.01)
(Continued)

(52) U.S. Cl.
CPC .......... *A61B 5/0042* (2013.01); *A61B 5/055* (2013.01); *A61B 5/165* (2013.01); *A61B 5/4064* (2013.01);
(Continued)

(58) Field of Classification Search
CPC ....... A61B 5/0042; A61B 5/055; A61B 5/165; A61B 5/4064; A61B 5/726; A61B 5/7267;
(Continued)

(56) References Cited

U.S. PATENT DOCUMENTS

| 2009/0136104 A1* | 5/2009 | Hajian | G01R 33/56 |
| | | | 382/128 |
| 2013/0137918 A1 | 5/2013 | Phillips et al. | |

(Continued)

FOREIGN PATENT DOCUMENTS

| CN | 106709907 A | * 5/2017 |
| WO | WO 2016/149808 | 9/2016 |
| WO | WO 2017/042635 | 3/2017 |

OTHER PUBLICATIONS

Waragai, M., Moriya, M., & Nojo, T. (2017). Decreased N-Acetyl Aspartate/Myo-Inositol Ratio in the Posterior Cingulate Cortex Shown by Magnetic Resonance Spectroscopy May Be One of the Risk Markers of Preclinical Alzheimer's Disease: A 7-Year Follow-Up Study. Journal of Alzheimer's disease : JAD, (Year: 2017).*

(Continued)

*Primary Examiner* — Catherine B Kuhlman
*Assistant Examiner* — Nicholas A Robinson
(74) *Attorney, Agent, or Firm* — HoustonHogle LLP

(57) ABSTRACT

A MRS (magnetic resonance spectroscopy or nuclear magnetic resonance NMR)-based PTSD (post-traumatic stress disorder) and mTBI (mild traumatic brain injury) diagnostic system and method uses MRS signals, already pre-processed by the MRS scanner software. The signals are collected in vivo from specific regions of the brain. A wavelet decomposition is applied to the MRS signals, and the amplitude of the wavelet coefficients and their location in the MRS signals are used as features for training diagnostic classifiers of disease states. These classifiers are identified through analysis of features of individuals whose health status is known. Once the classifiers are trained, patients can be diagnosed by using the same wavelet features extracted from in vivo MRS scans of their brain regions.

17 Claims, 13 Drawing Sheets

(51) Int. Cl.
 A61B 5/055 (2006.01)
 A61B 5/00 (2006.01)
 A61B 5/16 (2006.01)
(52) U.S. Cl.
 CPC ............ *A61B 5/726* (2013.01); *A61B 5/7267* (2013.01); *G16H 30/40* (2018.01); *G16H 50/20* (2018.01); *A61B 2576/026* (2013.01)
(58) Field of Classification Search
 CPC .......... A61B 2576/026; A61B 5/4088; G16H 50/20; G16H 30/40; G16H 50/70; G01R 33/46
 See application file for complete search history.

(56) References Cited

U.S. PATENT DOCUMENTS

| | | | | |
|---|---|---|---|---|
| 2017/0251985 | A1* | 9/2017 | Howard | A61B 5/369 |
| 2019/0113526 | A1* | 4/2019 | Pollard | A61K 31/138 |
| 2020/0277676 | A1* | 9/2020 | Hicks | A61B 5/4064 |

OTHER PUBLICATIONS

Stanwell P, Siddall P, Keshava N, Cocuzzo D, Ramadan S, Lin A, Herbert D, Craig A, Tran Y, Middleton J, Gautam S, Cousins M, Mountford C. Neuro magnetic resonance spectroscopy using wavelet decomposition . . . biochemical changes in people with spinal cord injury and pain. (Year: 2010).*
Waragai, M., Moriya, M., & Nojo, T. (2017). Decreased N-Acetyl Aspartate/Myo-Inositol Ratio in the Posterior Cingulate Cortex Shown by Magnetic Resonance Spectroscopy May Be One of the Risk Markers of Preclinical Alzheimer's Disease: A 7-Year Follow-Up Study. Journal of Alzheimer's disease : JAD, (Year: 2017).*
Kontos, A. P., Van Cott, A. C., Roberts, J., Pan, J. W., Kelly, M. B., McAllister-Deitrick, J., & Hetherington, H. P. (2017). Clinical and Magnetic Resonance Spectroscopic Imaging Findings in Veterans With Blast Mild Traumatic Brain Injury and Post-Traumatic Stress Disorder. Military medicine), (Year: 2017).*
Sreepada, L., Ladner, J., Liao, H., Rowland, B., Heaton, K., & Lin, A. (Apr. 26, 2017). Proton Magnetic Resonance Spectroscopy of Mild Traumatic Brain Injury in the Military, cds.ismrm.org. https://cds.ismrm.org/protected/17MProceedings/PDFfiles/2389.html. (Year: 2017).*
Amen, D.G., et al., "Functional Neuroimaging Distinguishes Post-trammatic Stress Disorder from Traumatic Brain Injury in Focused and Large Community Datasets," PLOS ONE, 1-16 (2015).
Anonymous, "Brain Scans Show PTSD Not Just Mental," https://www.cbsnews.com/news/brain-scans-show-ptsd-not-just-mental/, 1-5 (2009).
Anonymous, "Haar Function," Wolfram MathWorld, 1-2 (2018).
Anonymous, "Interpretting H-NMR Spectra," Chapter 13: Spectroscopy, 1-3 (2018).
Anonymous, "MRI Shows Brain Disruption in Children with PTSD," ScienceDaily, 1-4 (2016).
Anonymous, "Organic Chemistry/Spectroscopy," Wikibooks, 1-6 (2017).
Anonymous, "Pulse Sequence," 1-58 (2013).
Anonymous, "Test for the Significance of Relationships Between Two Continuous Variables," 1-2 (2018).
Anonymous, "Wavelet," Wolfram MathWorld, 1-2 (2018).
Anonymous, "Wavelets in NMR-Imaging," 1-25 (2006).
Arobone, E., "Introduction to Wavelets," 1-16 (2018).
Balakrishnama, S., et al., "Linear Discriminant Analysis—A Brief Tutorial," Institute for Signal and Information Processing, 1-9 (2018).
Barker, P.B., et al., "Quantitation of proton NMR spectra of the human brain using tissue water as an internal concentration reference," NMR in Biomedicine, 6(1): 89-94 (1993).
Combs, H.L., et al., "The effects of mild traumatic brain injury, post-traumatic stress disorder, and combined mild traumatic brain injury/post-traumatic stress disorder on returning veterans," Journal of Neurotrauma, 32(13): 956-966 (2015).

Daubechies, I., Ten lectures on wavelets. 1992: SIAM.
Drummond, K., "Neuroscientists Say Brain Scans Can Spot PTSD," https://www.wired.com/2010/01/brain-biomarker-could-be-the-key-to-ptsd-diagnosis/.
Galarneau, M.R., et al., "Traumatic brain injury during Operation Iraqi Freedom: findings from the United States Navy-Marine Corps Combat Trauma Registry," J. Neurosurg., 108(5): 950-957 (2008).
Guyon, I., et al., "An introduction to variable and feature selection," Journal of Machine Learning Research 3, 1157-1182 (2003).
Hornak, "The Basics of MRI," 1 (2018).
Hughes, K.C., et al., "Functional Neuroimaging Studies of Post-Traumatic Stress Disorder," Expert Rev. Neurother., 11(2): 275-285(2011).
Hull, A.M., "Neuroimaging Findings in Post-Traumatic Stress Disorder," British Journal ofPsychiatry, 181: 102-110 (2002).
Irvine, J.M., "New Methods for Biomarker Discovery from MRS Signals," Presentation to Imagine 2017, 1-19 (2017).
Karl, A., et al., "The Use of Proton Magnetic Resonance Spectroscopy in PTSD Research-Meta-Analyses of Findings and Methodological Review," Neuroscience and Biobehavioral Review, 34: 7-22 (2010).
Kierans, A.S. et al., "Myoinositol and glutamate complex neurometabolite abnormality after mild traumatic brain injury," Neurology, 82(6):521-528 (2014).
Kreis, R., "Issues of spectral quality in clinical 1H-magnetic resonance spectroscopy and a gallery of artifacts," NMR in Biomedicine, 17(6): 361-381 (2004).
Lin, A.P., et al., "Changes in the neurochemistry of athletes with repetitive brain trauma: preliminary results using localized correlated spectroscopy," Alzheimers Res Ther., 15, 7(1):13 (2015).
Liu, Z., et al., "WaVPeak: Picking NMR Peaks Through Wavelet-Based Smoothing and Volume-Based Filtering," Bioinformatics, 28(7): 914-920 (2012).
Maudsley, A.A., et al., "Mapping of Brain Metabolite Distributions by Volumentric Proton MR Spectroscopic Imaging (MRSI)," Magnetic Resonance in Medicine, 61: 548-559 (2009).
Mountford, C., et al., "Magentic Resonance Spectroscopy to Monitor Neurochemcial Changes in PTSD Study Protocol," 1-10 (2016).
Near, J., et al., "Frequency and phase drift correction of magnetic resonance spectroscopy data by spectral registration in the time domain," Magnetic Resonance in Medicine, 73(1): 44-50 (2015).
Proctor, S.P., "Automated Neuropyschological Assessment Metrics Version 4 (ANAM4): Select Psychometric Properties and Administration Procedures," U.S. Army Medical Research and Material Command, 1-47 (2015).
Provencher, S.W., "Estimation of metabolite concentrations from localized in vivo proton NMR spectra," Magnetic Resonance in Medicine, 30(6): 672-679 (1993).
Rodgers, C.T., et al., "Receive array magnetic resonance spectroscopy: whitened singular value decomposition (WSVD) gives optimal Bayesian solution," Magnetic Resonance in Medicine, 63(4): 881-891 (2010).
Rowland, B.C., et al., "Correcting for Frequency Drift in Clinical Brain MR Spectroscopy," J. Neuroimaging, 27: 23-28 (2017).
Saeidiborojeni, H.R., et al., "Better Evaluation of PTDS by MRI," Kermanshah University of Medical Science, 4(1): 1 (2012).
Saito, N., "Frequently Asked Questions on Wavelets," University of California, 1-10 (2014).
Scudellari, M., "Brain Scans to Distinguish Between Brain Injury and PTSD," IEEE Spectrum, 1-2 (2016).
Slobounov, S., et al., "Concussion in Athletics: Ongoing Clinical and Brain Imaging Research Controversies," Brain Imaging and Behavior, 6: 224-243 (2012).
Stoltenberg, J., et al., "Pulsed Nuclear Magnetic Resonance," 1-26 (2006).
Tate, A.R., et al., "Automated Feature Extraction for the Classification of Human in Vivo 13C NMR Spectra Using Statistical Pattern Recognition and Wavelets," MRM, 35: 834-840 (1996).
Villarreal, G., et al., "Proton Magnetic Resonance Spectroscopy of the Hippocampus and Occipital White Matter in PTSD: Preliminary Results," Can. J. Psychiatry, 47(7): 666-670 (2002).

(56) References Cited

OTHER PUBLICATIONS

Mariano, L., et al., "Virtual Biopsy: Distinguishing Post-Traumatic Stress for Mild Traumatic Brain Injury Using Magnetic Resonance Spectroscopy," IEEE Applied Imagery Patter Recognition Conference, Oct. 8-10, 2017.
Cocuzzo, D., et al., "In Vivo Brain Magnetic Resonance Spectroscopy: A Measure of Biomarker Sensitivity to Post-Processing Algorithms," Wireless and Communication Technologies for Bio-Information Systems, 2: 2900117 (2014).
Extended European Search Report dated Jan. 7, 2020, from European Patent Application No. 19187144.1, filed on Jul. 18, 2019. 9 pages.
Jiru, F., "Introduction to post-processing techniques," European Journal of Radiology, 67(2): 202-217 (2008).
Ng, T.S., et al., "Neuroimaging in repetitive brain trauma.," Alzheimers Res Ther., 6(10): 1-15 (2014).
Pijnappel, W., et al., "SVD-based quantification of magnetic resonance signals," Journal of Magnetic Resonance, 1992. 97(1): 122-134 (1992).
Rae, C.D., et al., "Glutathione in the human brain: Review of its roles and measurement by magnetic resonance spectroscopy," Anal Biochem., 529: 127-143 (2017).
Stanwell, P., et al., "Neuro magnetic resonance spectroscopy using wavelet decomposition and statistical testing identifies biochemical changes in people with spinal cord injury and pain." Neuroimage, 53(2): 544-552 (2010).

\* cited by examiner

| Binary Group Group1, Group 2 | Classification Accuracy (PCC) | Feature Locations | Potential Metabolites |
|---|---|---|---|
| 1. CIV, MIL | 79.2% | [2.12, 3.89] ppm | Glx: 2.12, Cre: 3.9 ppm |
| 2. MIL, mT | 90.0% | [3.78, 3.68, 1.85] ppm | Glx: 3.7, GABA: 1.89 ppm |
| 3. MIL, PT | 97.0% | [1.59, 1.39, 3.61] ppm | Lactate: 1.3 ppm |
| 4. mT, PT | 100% | [3.89, 1.14] ppm | Cre: 3.9 ppm |
| 5. mTPT, mT | 100% | [3.87, 1.61, 1.64] ppm | Cre: 3.9 ppm |
| 6. PT, mTPT | 100% | 1.29 ppm | Lactate: 1.3 ppm |

Fig. 6

METHOD AND SYSTEM FOR POST-TRAUMATIC STRESS DISORDER (PTSD) AND MILD TRAUMATIC BRAIN INJURY (MTBI) DIAGNOSIS USING MAGNETIC RESONANCE SPECTROSCOPY

GOVERNMENT SUPPORT

This invention was made with Government support under contract number W81XWH-10-1-0785, awarded by the U.S. Department of Defense. The Government has certain rights in the invention.

BACKGROUND OF THE INVENTION

MRS (magnetic resonance spectroscopy), also known as NMR (nuclear magnetic resonance) spectroscopy, is widely used to identify relative abundance of isotopes of atoms, with unpaired nuclear spin, in molecules. The fairly ubiquitous biological tissue imaging technique, MRI (magnetic resonance imaging), is based on MRS. The isotopes of interest in biochemistry, biology and organic chemistry include hydrogen-1, which is the most predominant, carbon-13, oxygen-17, sodium-23, and phosphorus-31, which are spin-aligned in their lowest stable quantum states in the presence of a magnetic field. If exposed to a sweep of radio frequency (RF) waves of the electromagnetic spectrum (e.g., around 500 megaHertz (MHz)), these nuclei can absorb energy from the electromagnetic field and hop (i.e., flip the spin orientation) to the next higher energy quantum state. MRS is a record of relative numbers of nuclei, which hop to the higher quantum state as the frequency is swept across a range.

The frequency at which a nucleus flips to the higher state varies according to the magnetic field experienced by the nucleus which in turn depends on the atom and its functional group (neighboring atoms). The dependence of the RF absorption frequency on the functional group allows H-atoms (and others listed above) in a molecule to be separated according to functional group. For example in benzyl alcohol, the H-atoms in the benzyl group, alkyl group and hydroxyl group can all be identified separately using MRS. That is because the effective magnetic field experienced by the H-atoms depends slightly on the countervailing magnetic field—counter to the applied field—of the electrons in the functional groups. The frequencies for absorption are converted into commonly used chemical shift ppm (parts per million).

In addition to traditional proton (H-1 or, equivalently, 1H or $^1H^+$)-based MRI for detecting injury to muscle tissues, proton-based MRS has over the past few years found new uses, e.g., in identifying PTSD (Post-Traumatic Stress Disorder), typically associated with harrowing battlefield experience, and traumatic brain injuries. An article by Hall, "Neuroimaging findings in post-traumatic stress disorder-Systematic Review", British Journal of Psychiatry, vol. 181, pp 102-110, 2003, reviews some MRS techniques for PTSD diagnosis. Another review article, Slobounov et al., "Concussion in athletics: ongoing clinical and brain imaging research controversies", Brain Imaging and Behavior, vol. 6, pp 224-243, 2012, also discusses concussion (also called mild Traumatic Brain Injuries or mTBI) detection techniques, including MRS methods.

A patent application, WO 2016/149808 A1 by Fraser et al., "Metabolomics profiling of central nervous system injury", September 2016, classifies nervous system injuries by studying MRS data, using PCA (principal component analysis). The injuries include mTBI and other "non-TBI" injuries.

Some other uses for MRS in separating groups of subjects are detailed by Tate et al., "Automated Feature Extraction for the Classification of Human in Vitro C-13 NMR spectra Using Statistical Pattern Recognition and Wavelets", Magnetic Resonance in Medicine, vol. 35, pp 834-840, 1996, which used C-13 MRS data from adipose tissue as a biomarker to classify individuals as vegans or omnivores with 94% success rate.

SUMMARY OF THE INVENTION

The current invention utilizes features extracted from proton-based MRS signals, acquired in vivo, and pattern recognition techniques to generate a diagnostic tool for PTSD and mTBI. Specifically, the invention can be used to diagnose if a patient has PTSD, mTBI, both, or neither, based on an MRS scan of the brain.

MRS technology provides a non-invasive in vivo technique for measuring the concentration of metabolites in the brain, thus serving as a "virtual biopsy" that can be used to monitor a range of neurological diseases. The traditional method for analyzing MRS data assumes that the signal arises from a known set of metabolites and finds the best fit to a collection of pre-defined basis functions representing this set. In contrast, the approach here does not make assumptions about the underlying metabolite population, and instead extracts a set of wavelet-based features from the entire MRS signal, and identifies a subset of these features that are indicators (biomarkers) of PTSD and/or mTBI. The features correspond to MRS signals from nuclei that are part of functional groups of metabolites.

The present approach has identified significant changes associated with PTSD and mTBI in many different regions of the MR spectrum, including regions corresponding to metabolites N-acetylaspartate (NAA), creatine (Cue), choline (Cho), glutamate (Glu), glutamine (Gln), gamma-amino butyric acid (GABA), myo-inositol (mI), lactate, and many others. Classifiers based on some of these features exhibit correct classification rates of nearly 80% or better in cross-validation, thus demonstrating the value of MRS as a non-invasive means of measuring biochemical signatures associated with PTSD and mTBI. See B. Rowland, L. Mariano, J. M. Irvine, A. P. Lin, "Correcting for frequency drift in clinical MR spectroscopy" Journal of Neuroimaging (JON-16-4688), Volume 27, Issue 1, January/February 2017, Pages 23-28.

The invention utilizes features extracted from a clean representation of raw MRS data as inputs to the diagnostic classifier. The clean MRS signal is the result of pre-processing raw MRS data acquired as Free Induction Decay (FID) signals during a MRS scan. The clean signals are obtained as standard output from MRS machines following pre-processing of acquired raw MRS data by the software that is packaged as an integral part of the MRS machine by the manufacturer. The software averages raw MRS time series data (e.g., at 2048 time steps) for each coil or channel of the machine. A typical value for the number of channels could be 32. The time series data for each channel is collected for a number of iterations or averages, e.g., 132. Therefore, for the numbers cited, a clean MRS signal would be a single time series curve obtained from "averaging" 32×132 time series signals. Finally, a FFT step converts time to frequency, which is then converted to ppm.

As mentioned, the system described in this invention starts with clean MRS signals, referred to simply as MRS signals. A clean MRS signal is in the ppm domain.

Each subject's MRS signal undergoes wavelet decomposition, and a subset of the resulting wavelet coefficients are used as features to classify subjects by their known health status (e.g., with PTSD, with mTBI or healthy). The wavelet coefficients are used to train binary classifiers, e.g., a Linear Discriminant Analysis (LDA) classifier (which is just one example), to distinguish between the groups, for each pairwise combination of groups of disease states. A feature selection approach, such as Sequential Forward Selection (SFS), is used to identify a subset of the wavelet coefficients that maximizes the ability of the classifier to accurately distinguish between the groups, as measured by a cross-validation test. The selected wavelet features correspond to regions of the MR spectrum that exhibit significant differences between disease states. Bio-chemical compounds, specifically fragments of them, with resonances in these regions of the spectrum are potential biomarkers for the diseases.

Once the locations and magnitudes of the distinguishing wavelet features have been identified, and the classifiers have been trained, they can be used to diagnose patients by obtaining their MRS signals followed by wavelet decomposition. The diagnostic process consists of extraction of wavelet features from the spectral locations previously identified by the feature selection process, and submission of the coefficients of the corresponding wavelets to the pre-trained classifiers for assigning the individual to one of the groups.

In general, according to one aspect, the invention features a magnetic resonance spectroscopy (MRS)-based diagnostic system for Post-Traumatic Stress Disorder (PTSD) and/or mild Traumatic Brain Injury (mTBI). The system comprises a MRS system for collecting MRS signals from patients and a computer system that creates and executes a diagnostic tool that uses wavelet analysis of the MRS signals to diagnose patients with Post-Traumatic Stress Disorder (PTSD) and/or mild Traumatic Brain Injury (mTBI) from the MRS signals.

Preferably, the computer system performs wavelet decomposition on the MRS signals to extract a set of wavelet features. Then, a subset of wavelet features are down-selected during a training phase of the diagnostic tool.

Typically, the training phase of the diagnostic tool is performed by analyzing MRS signals of subjects with PTSD and mTBI.

In the current embodiment, the diagnostic tool implements binary classifiers for PTSD and mTBI. The diagnostic classifiers distinguishing healthy control subjects from those with PTSD and/mTBI are trained using a subset of the wavelet features identified during the training phase.

Currently, the MRS signals are gathered from the Posterior Cingulate Gyrus (PCG).

In general, according to another aspect, the invention features a method for magnetic resonance spectroscopy (MRS)-based diagnosis for Post-Traumatic Stress Disorder (PTSD) and/or mild Traumatic Brain injury (mTBI). The method comprises collecting MRS signals from patients and using wavelet analysis of the MRS signals to diagnose patients with Post-Traumatic Stress Disorder (PTSD) and/or mild Traumatic Brain Injury (mTBI) from the MRS signals.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 6 is a table of classification accuracy, selected feature locations, and potential corresponding metabolites for binary classifiers derived from the data used to develop the classifier.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

Unless otherwise defined, all terms (including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1:
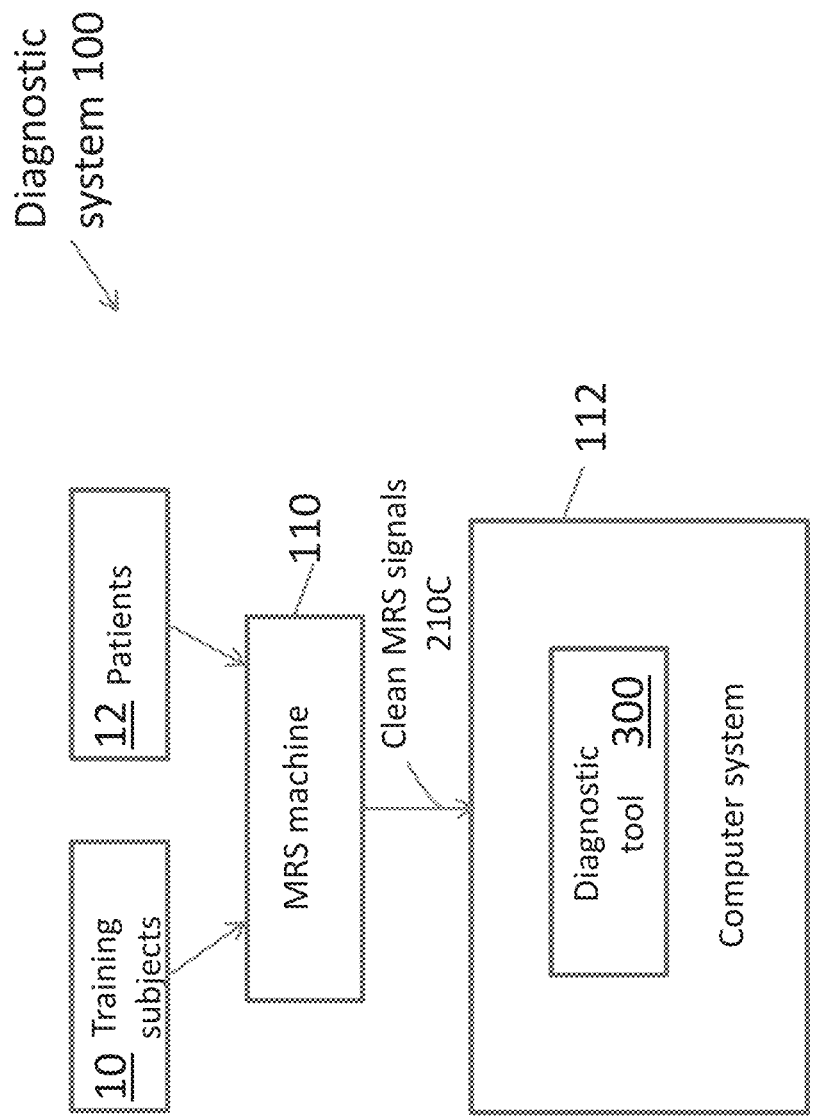
FIG. 1 is an overall block diagram of the PTSD and mTBI diagnostic system of the present invention.

FIG. 1 is an overall block diagram of a PTSD-mTBI diagnostic system 100 according to the principles of the present invention.

Figure 2A:
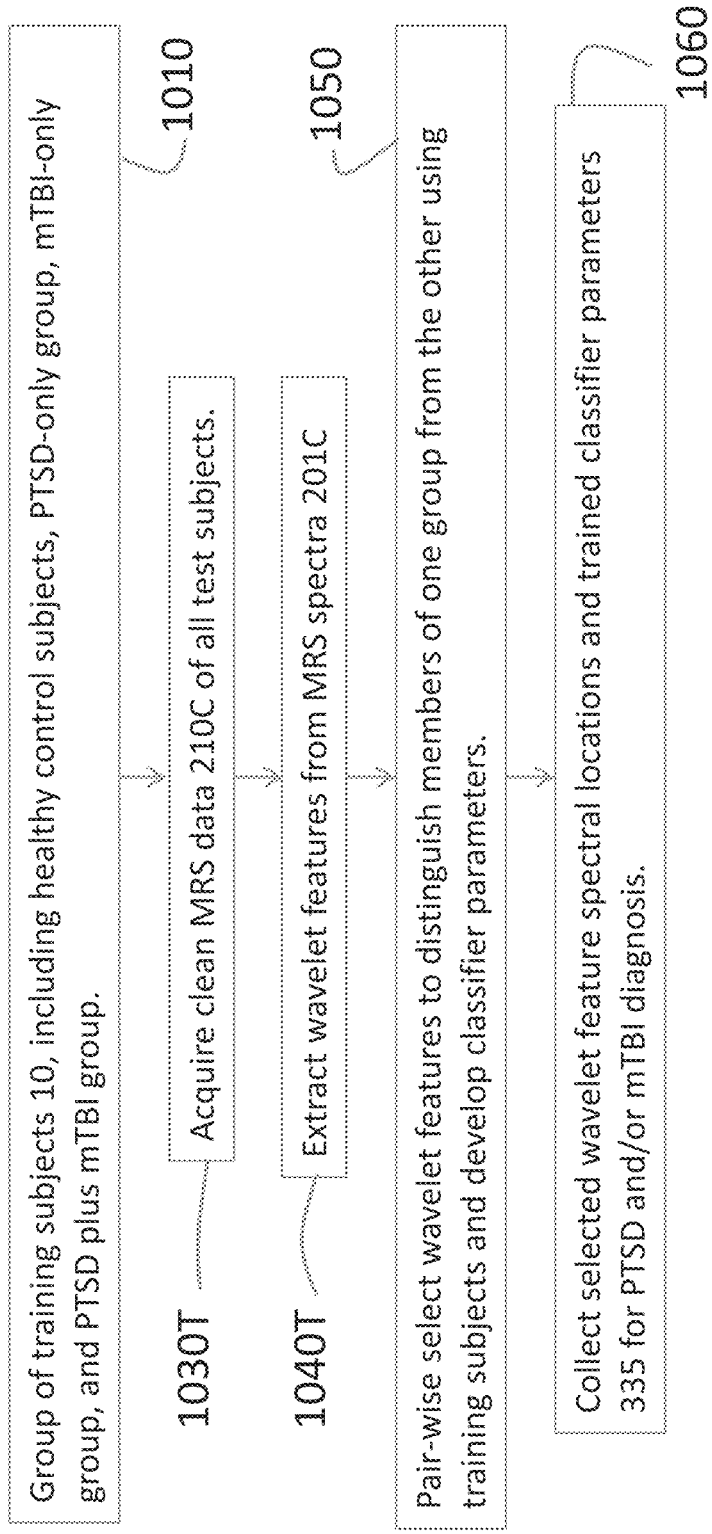
FIG. 2A is a flow diagram of steps for the design of the PTSD and mTBI diagnostic system using a set of training subjects.

The system 100 includes a diagnostic tool 300 that is installed and executed on a computer system 112. The tool 300 is trained by developing binary classifiers as shown in FIG. 2A. The classifiers are trained by analysis of MRS data 210C output from MRS machine 110 from brain regions of a training set of subjects 10 whose health status is known. Once the diagnostic system tool 300 is configured and trained, it can be used to diagnose patients 12 by obtaining and analyzing their MRS data as shown in FIG. 2B.

In principle, the same or different MRS machines can be used for both the training and diagnostic phases provided they can acquire and pre-process raw MRS data using identical instrument and pre-processing setting parameters. However, because of a current lack of hardware and software standardization of MRS machines, the machine 110 should ideally be the same make and model for both training and diagnostics phases of the tool 300.

Figure 2B:
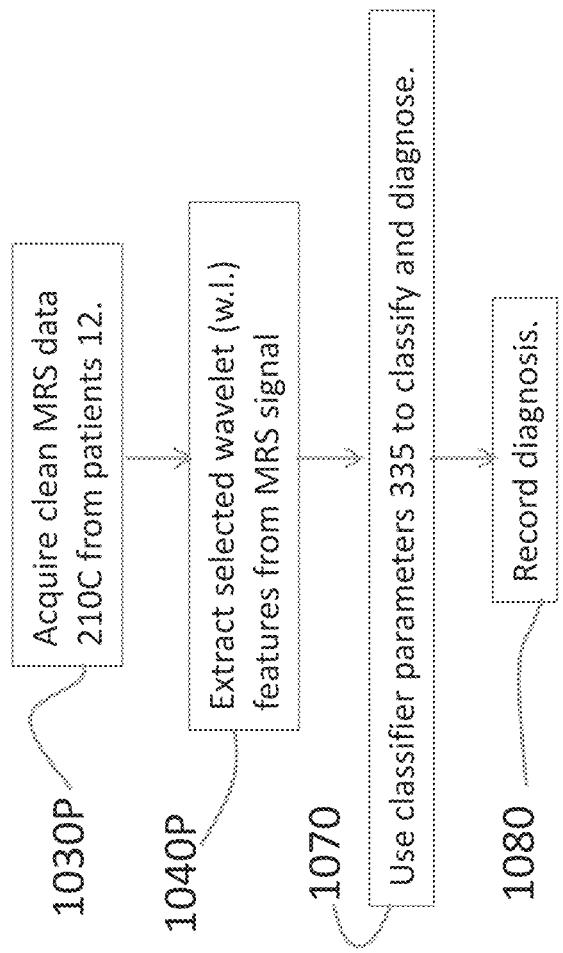
FIG. 2B is a flow diagram of steps for the use of the diagnostic system on patients.

FIGS. 2A and 2B are flow diagrams for training and configuration of the diagnostic tool 300.

As shown in FIG. 2A, the training of the diagnostics tool begins with step 1010 with a large representative training set of volunteers consisting of healthy civilians, healthy current or past military personnel (MP), MP with PTSD-only symptoms, MP with mTBI-only symptoms, and MP with both mTBI and PTSD symptoms. The training set subjects are assigned into 5 mutually exclusive groups (FIG. 3) based on their known health status: CIV (healthy civilians), MIL (MP who are healthy), mT (MP with mTBI-only), PT (MP with PTSD-only), and mTPT (MP with both PTSD and mTBI).

The next step 1030T is acquiring clean MRS signal 210C of the brain regions, a specific voxel or volume, of the subjects 10. In this system, the relevant brain region is Posterior Cingulate Gyrus (PCG) of volume=20 mm×20 mm×20 mm although other regions can be used. The MRS signal will be used for training.

The MRS signal 210C of each subject is then wavelet-analyzed to extract a set of wavelet features in step 1040T.

The five groups of the training set are coupled into pairs and the wavelet features of each subject in the pair are analyzed to determine distinguishing features that set members of one group apart from members the other group in the pair. Based on distinguishing wavelet features, classifiers are developed in step 1050.

In step 1060, the classifying wavelet features and parameters 335 (FIG. 5) are stored for later use for patient diagnosis.

FIG. 2B is a flow diagram for using the diagnosis system 100 on patients. The first step 1030P in diagnosing a patient is acquiring clean MRS data of a patient in the pool 12 from the same region of the brain as was used for training the classifiers. In step 1040P, wavelet coefficients are extracted from the MRS signal of the patients.

In step 1070, the amplitude values of the selected wavelet coefficients are compared against the pre-trained classifiers 335 (FIG. 5) incorporated in the diagnostic tool 300, which outputs and records the most likely diagnosis in step 1080.

Figure 3:
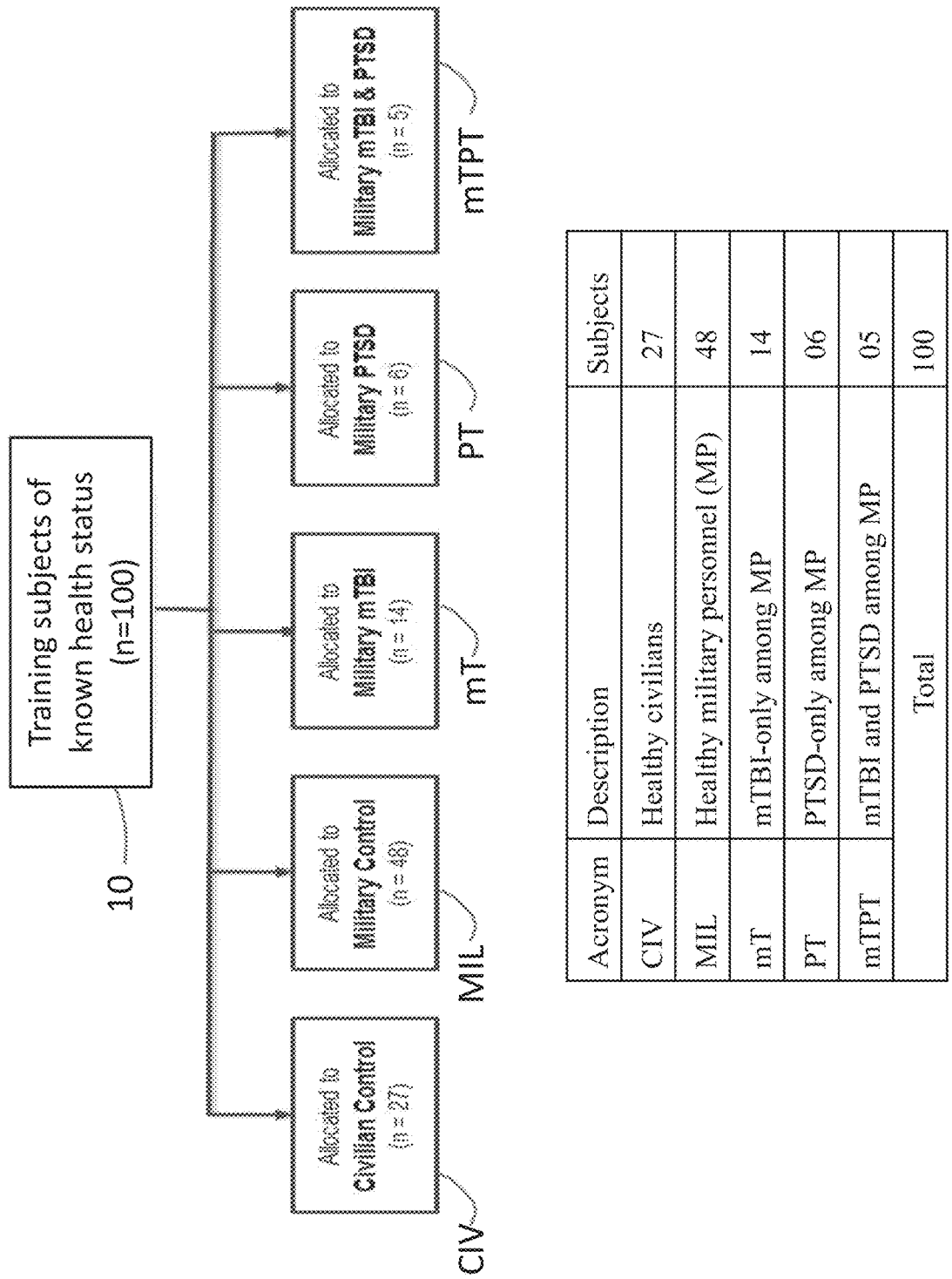
FIG. 3 shows the groupings of test subjects used in the design of the diagnostic system.

FIG. 3 shows the groupings of training subjects used in the study. A group of 100 test subjects 10 whose health status is known were divided into 5 mutually exclusive groups as shown. The test subjects consisted of civilian and military personnel (MP), and each was given extensive MRS scans and cognitive testing. The groups are: CIV (27 subjects, with no PTSD or mTBI), MIL (48 subjects, no PTSD or mTBI), PT (6 subjects, PTSD-only), mT (14 subjects, mTBI-only), mTPT (5 subjects, both mTBI and PTSD). The classification is based on self-reporting and prior diagnoses.

Figure 4:
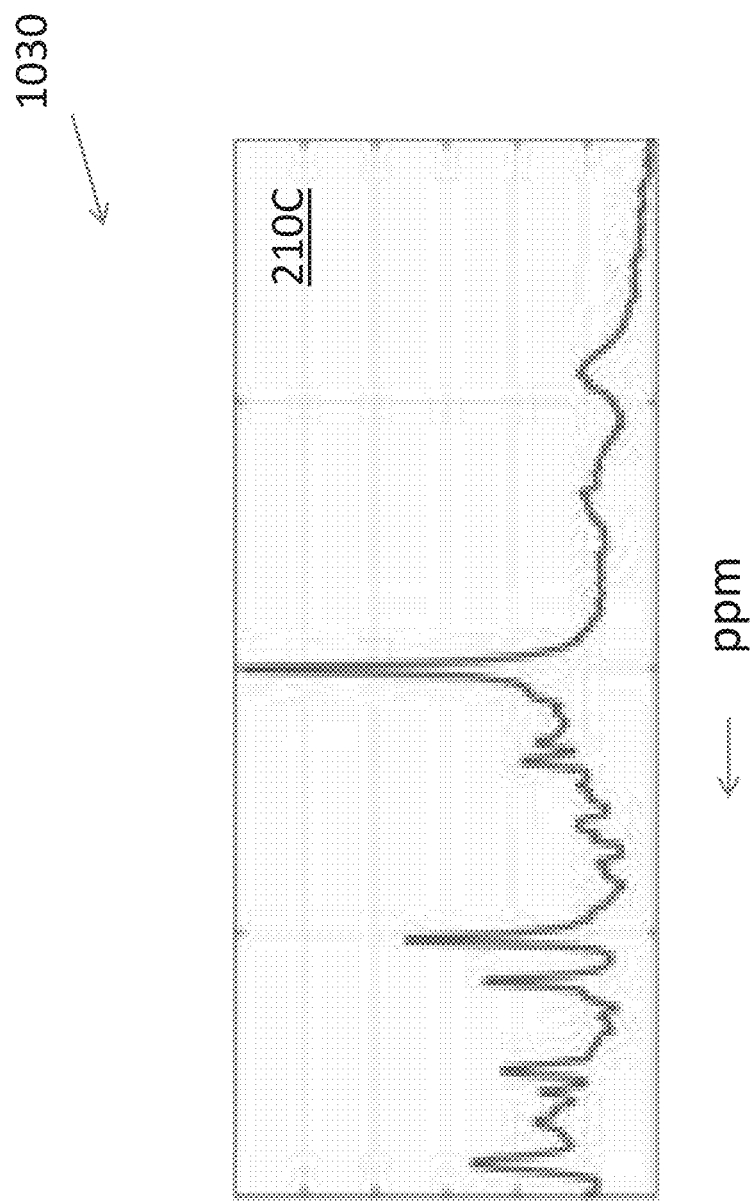
FIG. 4 is plot of a typical MRS spectrum (pre-processed from raw data) as a function of signal strength (arbitrary units) versus ppm.

FIG. 4 shows a typical MRS signal 210C used in step 1030, more specifically, 1030T (FIG. 2A) or 1030P (FIG. 2B).

Figure 5:
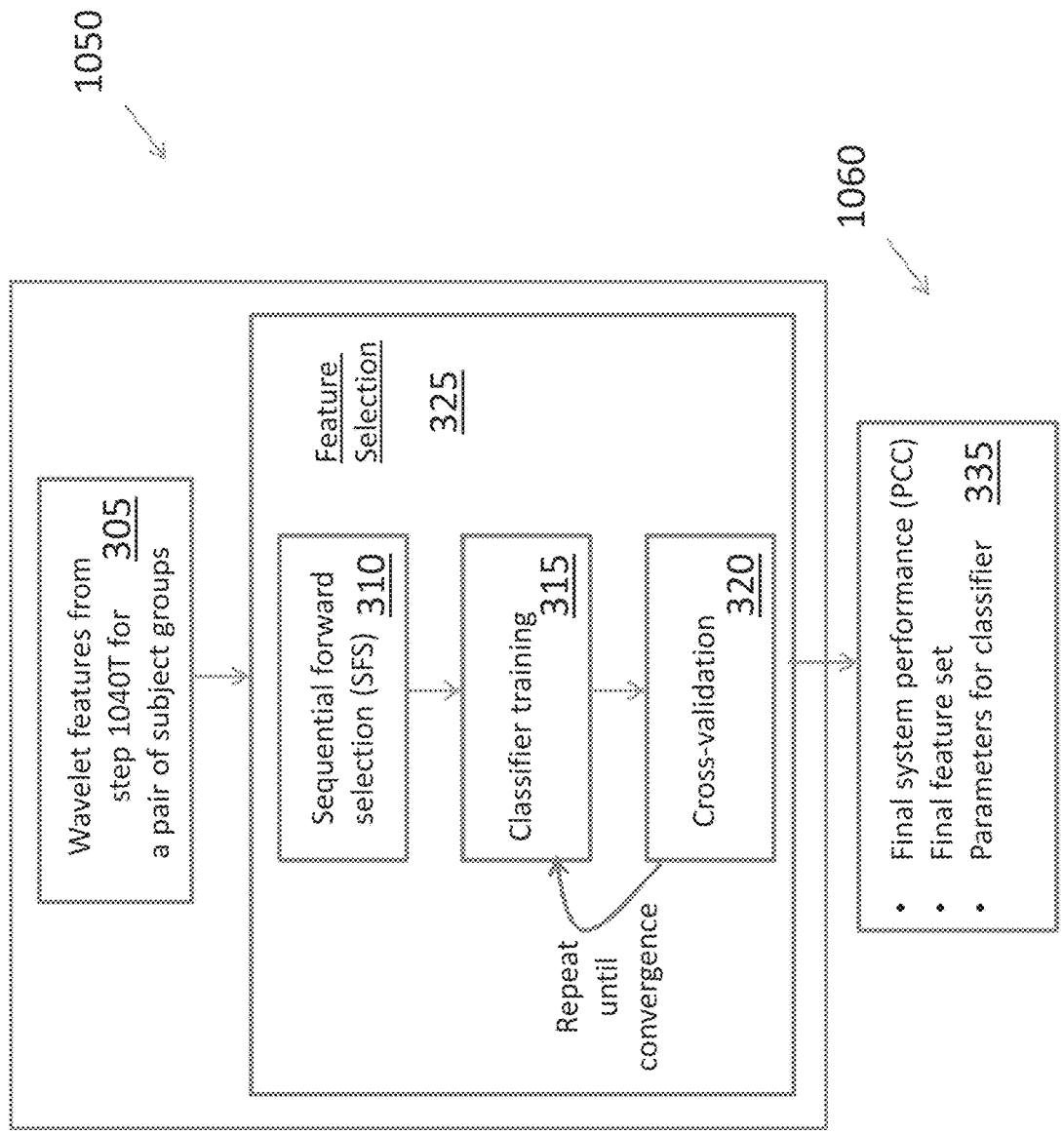
FIG. 5 shows the mathematical steps involved in the design of the system.

FIG. 5 shows the mathematical steps involved in the development of binary classifiers starting with wavelet features for a pair of two groups of subjects in step 305. The pairs chosen for this study are as listed in FIG. 6: (CIV, MIL); (MIL, mT); (MIL, PT); (mT, PT); (mTPT, MT); and (PT, mTPT). Other pairings could be made. The classifier is developed pair-wise one pair at a time.

The wavelet decomposition creates a large set of features that are potential markers for distinguishing between the groups, but only a subset of the most discriminating features are ultimately chosen for use in the diagnostic classifier. A wavelet feature of a MRS signal is the location in ppm of the wavelet function and its coefficient in the wavelet expansion of the signal. The coefficient is interpreted as the magnitude of the wavelet feature.

The wavelet features of the MRS signals of the subjects in each pair of groups are fed to the feature selection engine 325, which has three processes: Sequential Forward Selection (SFS) 310, classifier training 315 and cross-validation 320.

Starting with a large set of wavelet features 305 and down-selecting them for classification 325 constitutes step 1050 of FIG. 2A.

A Sequential Forward Selection (SFS) scheme 310 (see Gyoun and Elisseeff, "An introduction to variable and feature selection", Journal of Machine Learning Research, vol. 3, pp. 1157-1182. 2003) is used to identify optimal subsets of features for discriminating between each group in a pair. In SFS, feature selection begins by assessing the performance of the classifier 315 for each feature individually. In this case, performance is measured as the average Percent Correct Classification (PCC) from multiple iterations of a k-fold cross-validation test of the classifier 320, although other optimization criteria can be used depending on the requirements of the final system. The single feature that has the highest PCC is added to the subset. Additional features are added one at a time, and the performance of the combined feature set is recomputed. If the addition of the new feature increases the PCC, that feature is added to subset, and the process repeats until adding new features to the subset no longer increases the PCC of the classifier (convergence) 325. An LDA classifier was used for this analysis, but there are many other binary classifiers that can be used in the same feature selection scheme.

This process 325 outputs a final set 335 of selected classifying features for pairs, the PCC of those features, and a set of classifier parameters derived from the features. They can then be used for diagnosis of new patients. Collecting the items in 335 for diagnostics is step 1060 in FIG. 2A.

In the current embodiment, the feature extraction approach does not use information regarding locations of known metabolites. Therefore, the features identified through SFS may not map directly to compounds with known functionality in the brain. However, analysis of the dataset used to develop this technology demonstrated that features selected through the feature selection/classifier training process did correspond to metabolites that have previously demonstrated sensitivity to neurological conditions as shown in FIG. 6 under column heading "Potential Metabolites."

FIG. 6 is a table showing locations of the wavelet features, in ppm, selected by the SFS feature selection scheme. The features can be used to classify (i.e., distinguish) each member of six pairs: 1. (CIV, MIL); 2. (MIL, mT); 3. (MIL, PT); 4. (mT, PT); 5. (mTPT, mT); and 6. (PT, mTPT). The table contains the average Percent Correct Classification (PCC) from all iterations of the cross-validated SFS (sequential forward selection) search for the top 3 (at most) features selected for each binary classifier. The top feature locations in ppm are listed under the "Feature Locations" column. Known metabolites found in the regions around the selected features are listed under the "Potential Metabolites" column.

The $1^{st}$ entry suggests that feature magnitudes at 2.12 and 3.89 ppm can distinguish CIV and MIL groups with 79% certainly. The $2^{nd}$ entry suggests that features at 3.78, 3.68 and 1.85 ppm can be used to distinguish MIL and mT groups with 90% certainty. Finally, the $3^{nd}$ entry suggests that features at 1.59, 1.39 and 3.61 ppm can be used to distinguish MIL and PT groups with 97% certainty. The $4^{th}$ entry says that using the magnitudes (coefficients) of wavelet features located in the MRS scans at 3.89 and 1.14 ppm, one can distinguish patients with mTBI-only and PTSD-only with 100% certainty. The $5^{th}$ entry suggests that using magnitudes of features at 3.87, 1.61 and 1.64 ppm, patients suffering from both mTBI and PTSD can be distinguished from those suffering from mTBI-only with 100% certainty. Finally, the $6^{th}$ entry suggests that using the magnitude of feature at 1.29 ppm, one can distinguish patents suffering from both mTBI and PTSD from those suffering PTSD-only.

It is important to point out that the distinguishing features, located as indicated in FIG. 6, must be considered collectively for each pair for distinguishing each group of the pair.

FIGS. 7A-7F depict scatter plots of the features selected by each of the six binary group classifiers identified in the table of FIG. 6. The plots show the magnitudes of the classifying features along the axes which are labeled by the feature locations in ppm. In each plot, points belonging to one group are distinguished from those belong to the second group. In all cases, there are visually distinct differences in magnitude clusters between the points of each group for the features selected by the SFS process.

It should be noted that the number of subjects that was used for the classification analysis differs from the numbers shown in FIG. 3. Due to issues with data quality, data from some of the subjects had to be excluded from analysis.

Figure 7A:
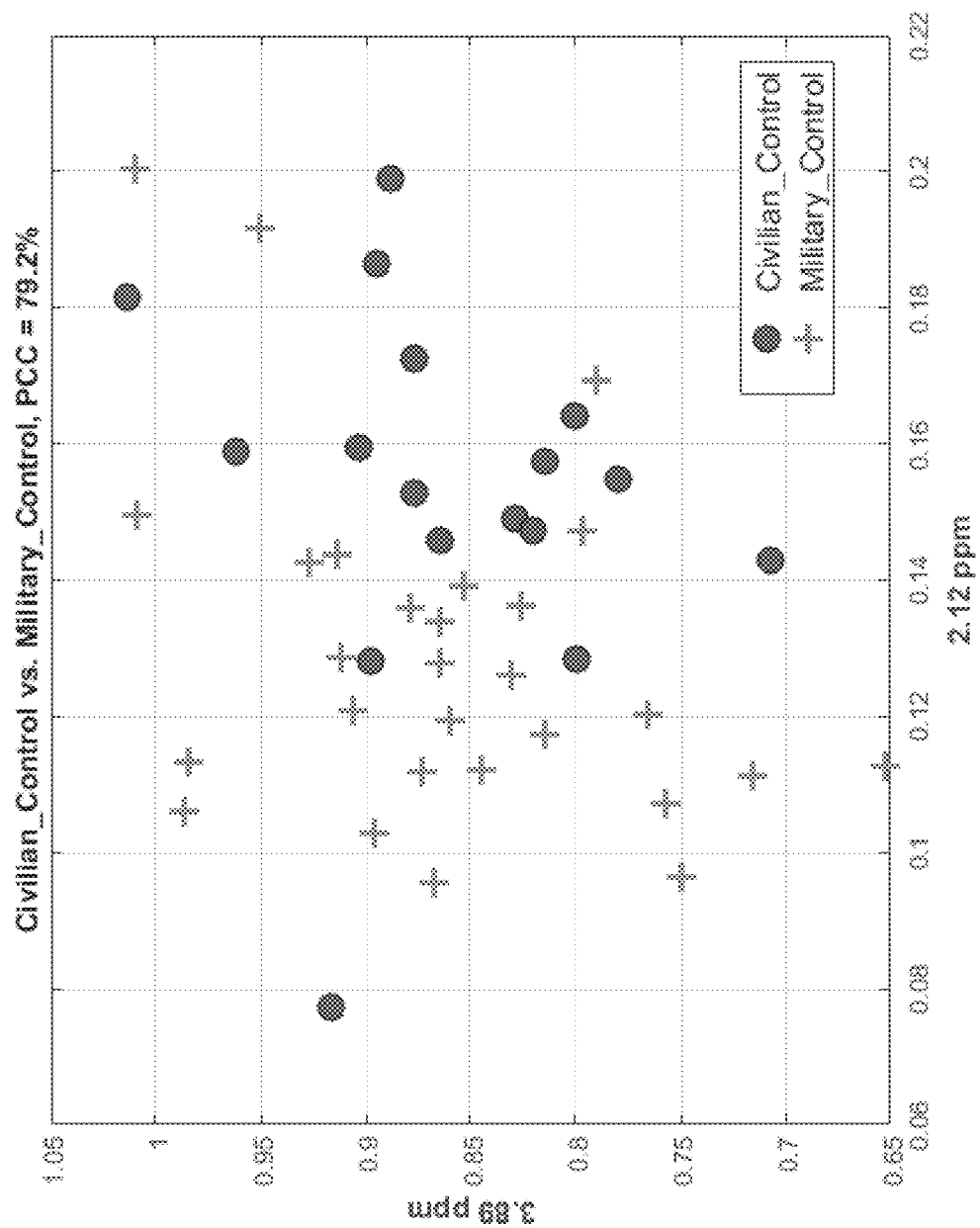
FIGS. 7A-7F are scatter plots depicting the magnitudes of the features selected by each of the classifiers for six different pairs of binary classifiers of FIG. 6.

In FIG. 7A, corresponding to the first entry of FIG. 6 for distinguishing CIV and MIL groups, the features are located at 2.12 and 3.89 ppm, which are the two axes of the figure. The coordinates of the plotted points correspond to the feature magnitudes of the CIV and MIL members. The "+" sign indicates MIL group members. The filled circle indicates CIV group members.

Figure 7B:
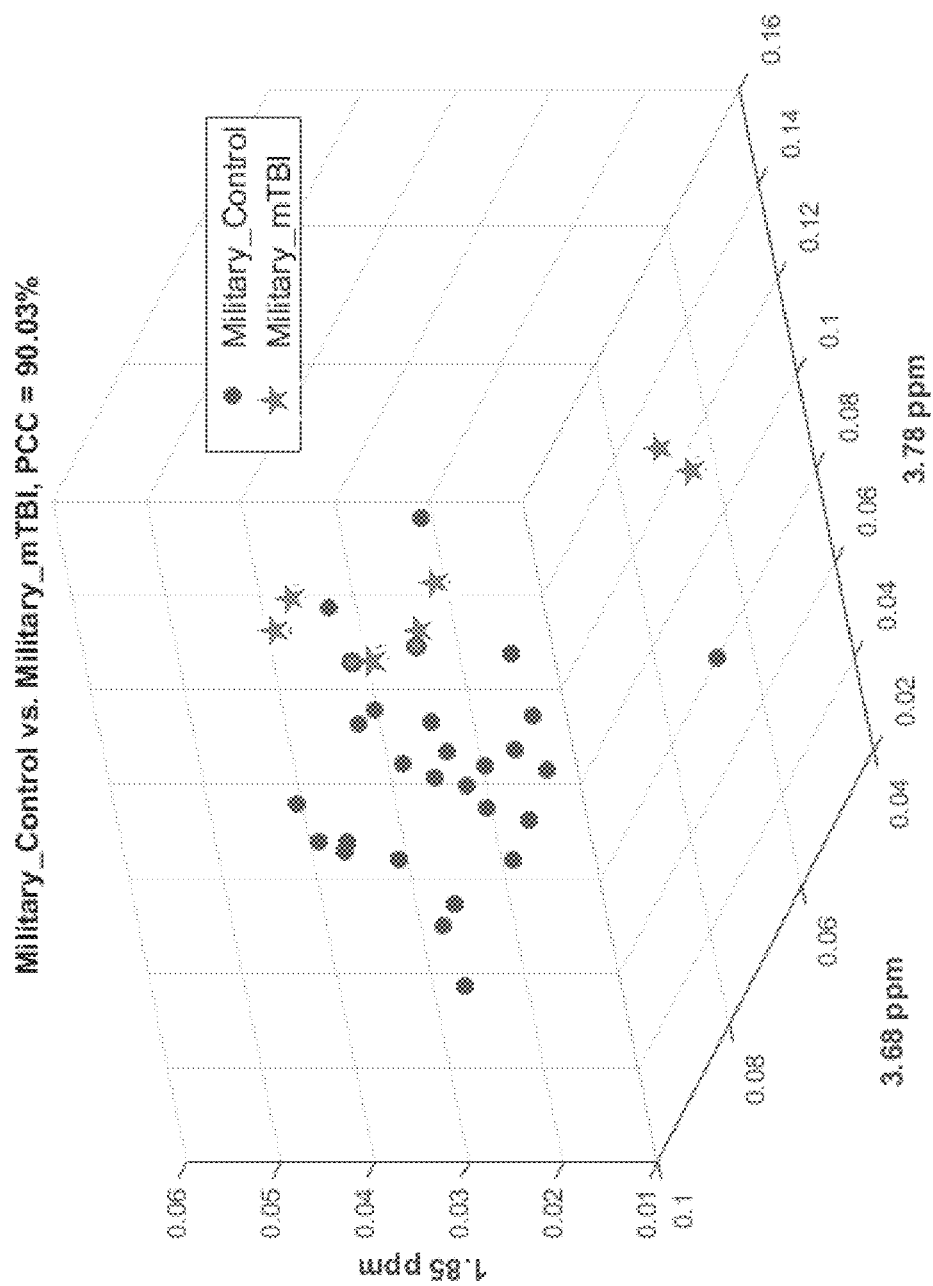

FIG. 7B, corresponding to the second entry of FIG. 6 for distinguishing mT and MIL groups, has three features. Therefore FIG. 7B has three axes corresponding to ppm locations of the three features. In this figure mT group members ("*" for mT) are distinct by feature magnitudes from MIL group members (filled circle).

Figure 7C:
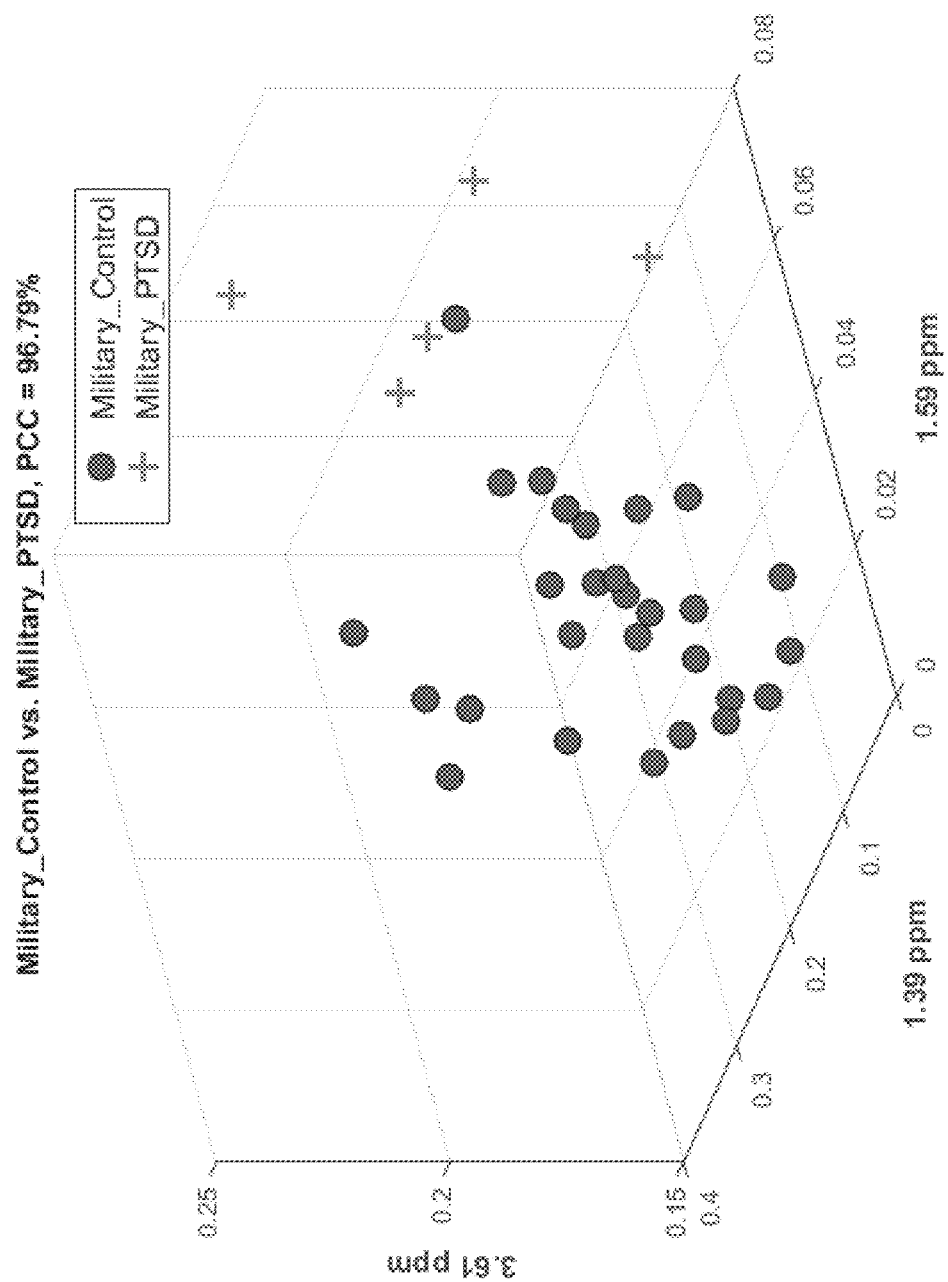

FIG. 7C, corresponding to the $3^{rd}$ entry of FIG. 6 for PT and MIL, has three features. Therefore this figure has three axes corresponding to locations of the three features. Here also PT group members ("+" sign) are distinct by feature magnitudes from the MIL group members (filled circle).

Figure 7D:
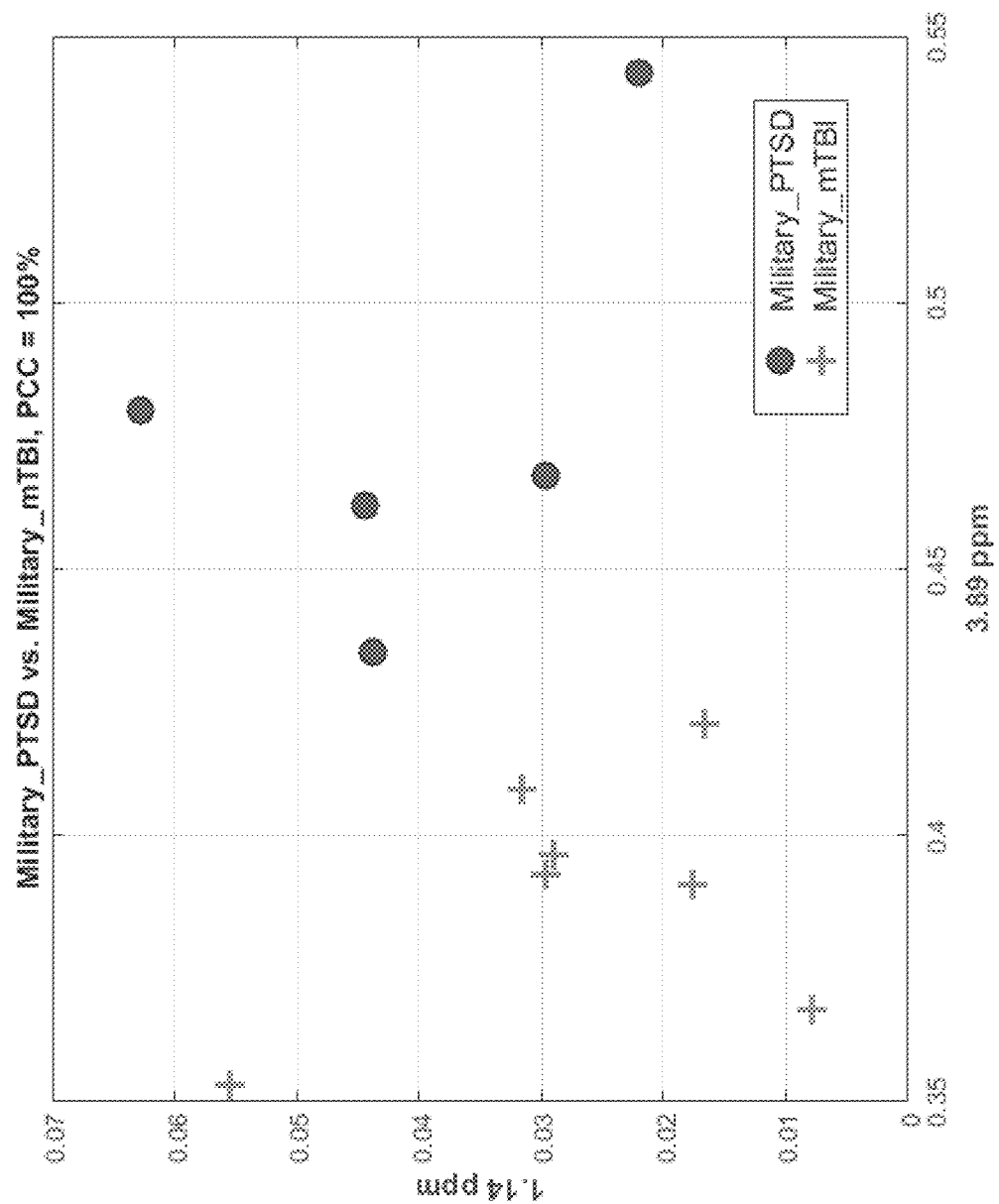

FIG. 7D, corresponding to the $4^{th}$ entry of FIG. 6 for PT and mT group members, has two features. Here again mT members ("+" sign) are clearly distinguishable from PT members (filled circle).

Figure 7E:
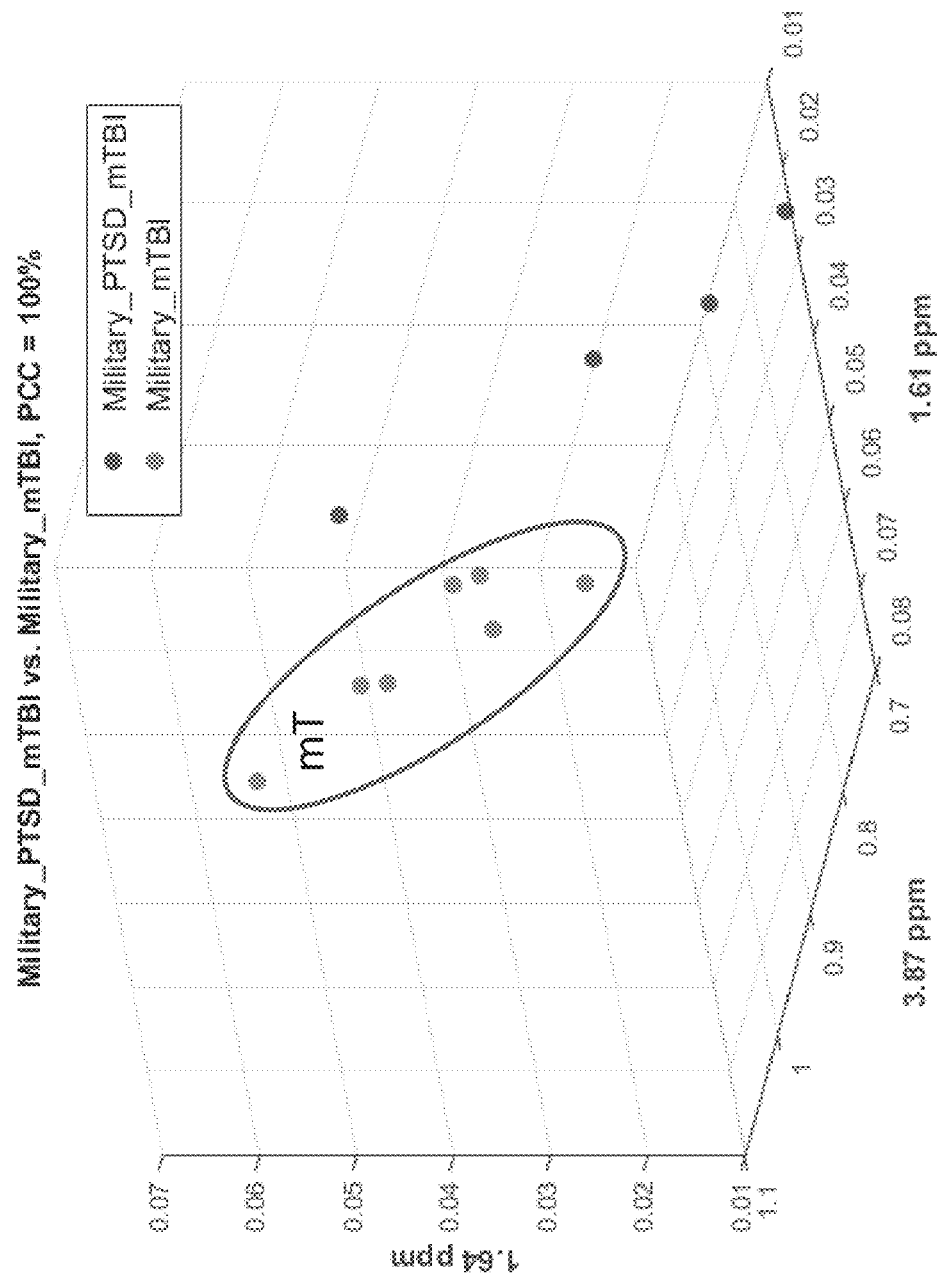

FIG. 7E, corresponding to the $5^{th}$ entry of FIG. 6 for mT and mTPT, has three features. Here again mT members (enclosed in an oval) are clearly distinguishable from mTPT members.

Figure 7F:
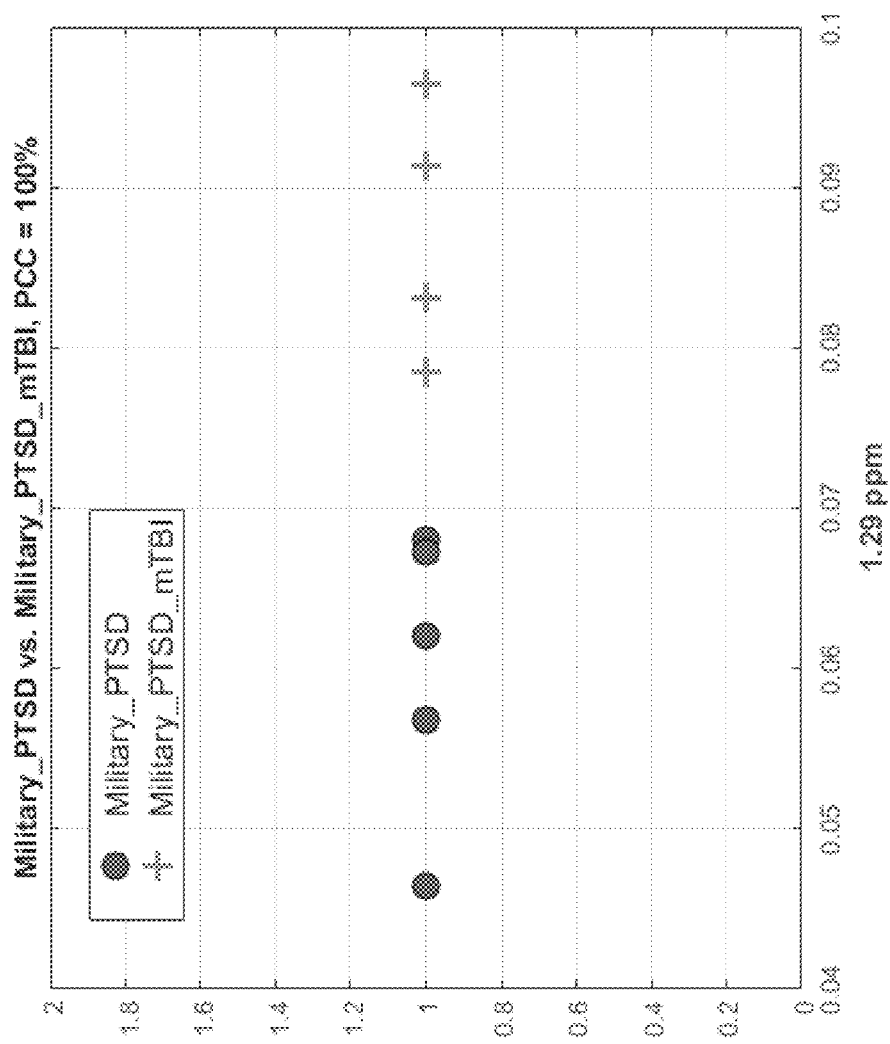

FIG. 7F, corresponding to the $6^{th}$ entry of FIG. 6, is a single feature classifier for PT and mTPT. The mTPT members ("+" sign) are bunched to the right, whereas PT group members are bunched to the left. In this plot, the vertical axis has no significance.

Although the method described in the invention is sound, supporting evidence for classifying features would benefit from using many more training subjects in the study.

While the subject population used to develop this technology included military and civilian personnel, the training methodology used to develop the diagnostic classifiers can be applied to any population of individuals with known health status.

Overall, the diagnostic tool has demonstrated the value of MRS as a non-invasive means of measuring brain biochemistry that has enough sensitivity to reveal significant, distinct, metabolic changes associated with PTSD and mTBI. Using feature extraction, classification, and feature selection, the invention has been able to identify many regions in the ID NMR spectra that can be used to distinguish subject sub-populations. While the wavelet-based feature extraction approach is data-driven and agnostic to the presence of known metabolites in any region of the spectrum, the statistical and classification analysis pinpointed spectral regions containing metabolites that have been previously implicated in neurodegenerative and neuro-inflammatory diseases. The results on this small sample size are promising for applying this data-driven biomarker-discovery approach to the study of other disease states.

While this invention has been particularly shown and described with references to preferred embodiments thereof, it will be understood by those skilled in the art that various changes in form and details may be made therein without departing from the scope of the invention encompassed by the appended claims.

What is claimed is:

1. A magnetic resonance spectroscopy (MRS)-based diagnostic system for Post-Traumatic Stress Disorder (PTSD) and/or mild Traumatic Brain Injury (mTBI), comprising:
  a MRS system for collecting MRS signals from a Posterior Cingulate Gyrus (PCG) of patients; and
  a computer system that creates and executes a diagnostic tool that uses wavelet analysis of the MRS signals from the PCG to diagnose patients with Post-Traumatic Stress Disorder (PTSD) and/or mild Traumatic Brain Injury (mTBI) from the MRS signals, wherein the computer system generates clean MRS signals by averaging the MRS signals for each coil of the MRS system, performs wavelet decomposition on the clean MRS signals and then extracts wavelet features from the clean MRS signals as inputs to the diagnostic tool, wherein the wavelet features are locations in ppm (parts per million) and coefficients in a wavelet expansion of the clean MRS signals and wherein in a training phase, the diagnostic tool creates a subset of wavelet features determined by adding a wavelet feature to the subset that has a highest performance for discrimination and then adds additional wavelet features to the subset when the additional wavelet features increase the performance of the subset, wherein the diagnostic tool employs the wavelet features at 3.89 and 1.14 ppm to diagnose between mTBI and PTSD.

2. A system as claimed in claim 1, wherein the training phase of the diagnostic tool is performed by analyzing MRS signals of subjects with PTSD and mTBI.

3. A system as claimed in claim 1, wherein the diagnostic tool implements binary classifiers for PTSD and mTBI.

4. A system as claimed in claim 1, wherein the computer system trains diagnostic classifiers distinguishing healthy control subjects from those with PTSD and/or mTBI are trained using the subset of the wavelet features identified during the training phase.

5. A system as claimed in claim 1, wherein the diagnostic tool implements classifiers distinguishing healthy controls subjects from those with PTSD and/or mTBI learned in the training.

6. A system as claimed in claim 1, further comprising characterizing metabolites including N-acetylaspartate (NAA), creatine (Cre), choline (Cho), glutamate (Glu), glutamine (Gln), gamma-amino butyric acid (GABA), myo-inositol (mI), and lactate.

7. A system as claimed in claim 1, wherein the subset of wavelet features with a highest performance for discrimination are determined by measuring performance as an average Percent Correct Classification (PCC) from multiple iterations of a k-fold cross-validation test of the wavelet features.

8. A system as claimed in claim 1, wherein the diagnostic tool employs the wavelet features at 3.87, 1.61 and 1.64 ppm to diagnose between both mTBI and PTSD and mTBI-only.

9. A system as claimed in claim 1, wherein the diagnostic tool employs the wavelet features at 1.29 ppm to diagnose between both mTBI and PTSD and PTSD-only.

10. A system as claimed in claim 1, wherein the training phase of the diagnostic tool is performed by analyzing MRS signals of subjects with PTSD and mTBI and wherein the diagnostic tool implements binary classifiers for PTSD and mTBI.

11. A method for magnetic resonance spectroscopy (MRS)-based diagnosis for Post-Traumatic Stress Disorder (PTSD) and/or mild Traumatic Brain Injury (mTBI), comprising:

collecting MRS signals from a Posterior Cingulate Gyrs (PCG) of patients with an MRS system; and using wavelet analysis of the MRS signals from the PCG to diagnose patients with Post-Traumatic Stress Disorder (PTSD) and/or mild Traumatic Brain Injury (mTBI) from the MRS signals by generating clean MRS signals by averaging the MRS signals for each coil of the MRS system, performing wavelet decomposition on the clean MRS signals, then extracting wavelet features from the clean MRS signals, the wavelet features being locations in ppm (parts per million) and coefficients in a wavelet expansion of the clean MRS signals, creating a subset of wavelet features determined by adding a wavelet feature to the subset that has a highest performance for discrimination, and then adding additional wavelet features to the subset when the additional wavelet features increase the performance of the subset to create a final subset of wavelet features, wherein the wavelet features at 3.89 and 1.14 ppm are employed to diagnose between mTBI and PTSD.

12. A method as claimed in claim 11, further comprising implementing binary classifiers for PTSD and mTBI.

13. A method as claimed in claim 11, wherein diagnostic classifiers distinguishing healthy control subjects from those with PTSD and/or mTBI are trained using the final subset of the wavelet features.

14. A method as claimed in claim 11, wherein the wavelet features with a highest performance for discrimination are determined by measuring performance as an average Percent Correct Classification (PCC) from multiple iterations of a k-fold cross-validation test of the wavelet features.

15. A method as claimed in claim 11, wherein the wavelet features at 3.87, 1.61 and 1.64 ppm are employed to diagnose between both mTBI and PTSD and mTBI-only.

16. A method as claimed in claim 11, wherein the wavelet features at 1.29 ppm are employed to diagnose between both mTBI and PTSD and PTSD-only.

17. A method as claimed in claim 11, further comprising analyzing MRS signals of subjects with PTSD and mTBI and implementing binary classifiers for PTSD and mTBI.

* * * * *